United States Patent
McGrath

(10) Patent No.: US 11,547,592 B1
(45) Date of Patent: Jan. 10, 2023

(54) ARM SUPPORT APPARATUS

(71) Applicant: Steven McGrath, Napa, CA (US)

(72) Inventor: Steven McGrath, Napa, CA (US)

(*) Notice: Subject to any disclaimer, the term of this patent is extended or adjusted under 35 U.S.C. 154(b) by 0 days.

(21) Appl. No.: 17/830,081

(22) Filed: Jun. 1, 2022

Related U.S. Application Data

(60) Provisional application No. 63/294,588, filed on Dec. 29, 2021.

(51) Int. Cl.
| | |
|---|---|
| *A61F 5/37* | (2006.01) |
| *A61F 5/058* | (2006.01) |
| *A61F 5/02* | (2006.01) |
| *A61F 5/01* | (2006.01) |

(52) U.S. Cl.
CPC .............. *A61F 5/3723* (2013.01); *A61F 5/02* (2013.01); *A61F 5/05858* (2013.01); *A61F 5/37* (2013.01); *A61F 5/3715* (2013.01); *A61F 5/3753* (2013.01); *A61F 2005/0167* (2013.01)

(58) Field of Classification Search
CPC ...... A61F 5/0193; A61F 5/02; A61F 5/05841; A61F 5/05858; A61F 5/37; A61F 5/3715; A61F 5/3723; A61F 5/373; A61F 5/3738; A61F 5/3753; A61F 2005/0167; A61F 2005/0183
See application file for complete search history.

(56) References Cited

U.S. PATENT DOCUMENTS

| | | | |
|---|---|---|---|
| 1,660,721 A | 2/1928 | Schrag | |
| 4,373,517 A * | 2/1983 | Criscuolo | ............. A61F 5/3753 602/5 |
| 5,111,983 A | 5/1992 | Simmons et al. | |
| 5,487,724 A | 1/1996 | Schwenn | |
| 5,665,058 A * | 9/1997 | Young | ................... A61F 5/3753 602/20 |
| 6,039,707 A | 3/2000 | Crawford et al. | |
| 7,189,213 B1 | 3/2007 | Weber | |
| 7,300,410 B1 | 11/2007 | Weber | |
| 7,749,179 B2 | 7/2010 | Hargrave et al. | |
| 7,819,827 B2 | 10/2010 | Pellinen | |
| 8,043,241 B2 | 10/2011 | Goumas | |
| 8,273,041 B2 | 9/2012 | Goumas | |
| 8,992,451 B2 | 3/2015 | Fout | |
| 9,204,989 B2 | 12/2015 | Begon et al. | |
| 10,123,899 B1 | 11/2018 | Theriot et al. | |
| 10,610,400 B1 * | 4/2020 | Krenzel | .................. A61F 5/013 |
| 10,736,767 B2 | 8/2020 | Boileau et al. | |

(Continued)

*Primary Examiner* — Keri J Nelson
(74) *Attorney, Agent, or Firm* — Staniford Tomita LLP; Paul K. Tomita

(57) ABSTRACT

The arm brace supports the arm weight. The arm brace has a soft elastic arm pad that partially surrounds and protects the forearm. The arm pad is secured to a platform that is supported by a brace structure that is secured to the waist and the thigh of the patient. The weight of the arm can be supported by the hips. The brace is releasably coupled to a side of a patient's torso and thigh with belts. The brace provides rotational stability that immobilizes the arm regardless of the position of the patient. The brace has a hinge adjacent to the hip that allows the brace to immobilize the forearm while the patent dynamically moves during activities including: standing, walking, sitting, and lying down. The hand extends out from the brace so the user can perform activities such as eating, typing, and grasping.

18 Claims, 8 Drawing Sheets

(56) References Cited

U.S. PATENT DOCUMENTS

| | | |
|---|---|---|
| 10,898,362 B2 | 1/2021 | Bejarano |
| 10,912,667 B1 | 2/2021 | Sickles et al. |
| 10,918,513 B2 | 2/2021 | Golden et al. |
| 2001/0032365 A1* | 10/2001 | Sramek ................ A47C 20/021 5/652 |
| 2012/0222219 A1* | 9/2012 | Pusca .................... A47C 16/00 5/655.3 |
| 2020/0113721 A1 | 4/2020 | Kilbey et al. |
| 2020/0113724 A1 | 4/2020 | Kilbey |
| 2020/0253776 A1 | 8/2020 | Boileau et al. |
| 2020/0368057 A1 | 11/2020 | Boileau et al. |
| 2021/0228397 A1 | 7/2021 | Gildersleeve et al. |

* cited by examiner

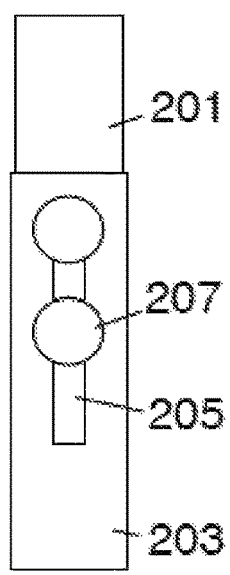 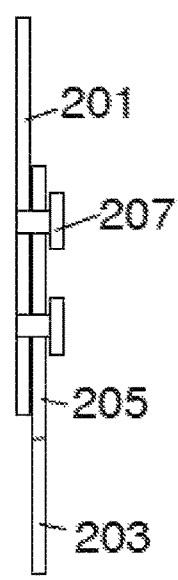 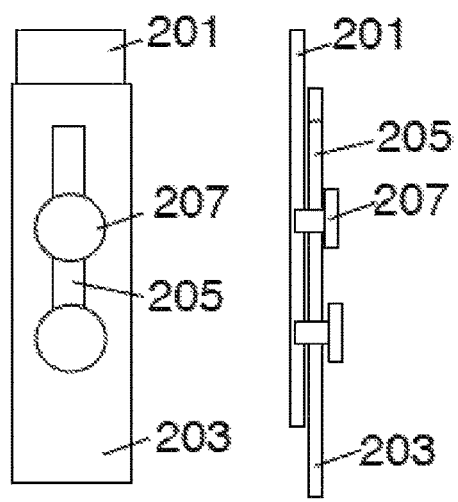 
FIG. 9  FIG. 10  FIG. 11  FIG. 12
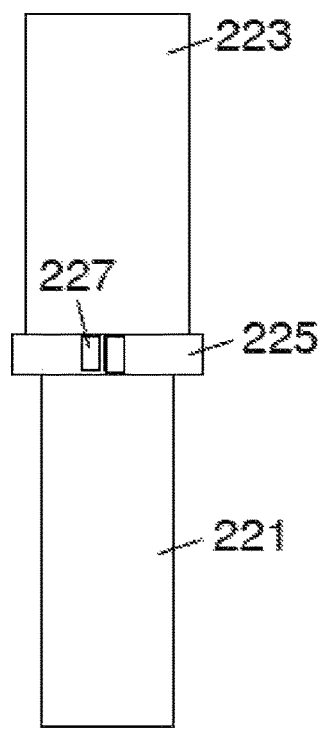 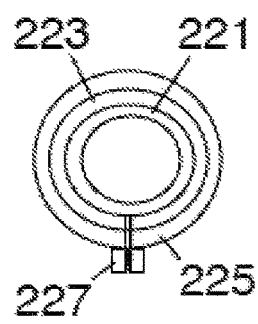
FIG. 14
FIG. 13

ARM SUPPORT APPARATUS

CROSS REFERENCE TO RELATED APPLICATIONS

This application claims priority to U.S. Provisional Patent Application No. 63/294,588, "Load Bearing Shoulder Immobilizer And Arm Support, Without The Need For A Shoulder Strap," filed Jan. 5, 2022 which is hereby incorporated by reference in its entirety.

FIELD OF INVENTION

The present invention is directed towards a brace for arm and/or shoulder immobilization.

BACKGROUND

When people injure their arms and/or shoulders, it can be necessary to immobilize the arm to protect the limb and supports the weight of the arm to allow the arm and/or shoulder to heal. Similarly, when people have arm or shoulder surgery, it can be necessary to immobilize the arm to allow the arm and/or shoulder to recover from the surgery. The most common immobilization devices are arm braces and slings. However, there are many drawbacks with existing arm braces and slings.

Many prior art braces and slings require a strap that wraps around the neck or opposing shoulder which can be uncomfortable. Shoulder slings as well as the majority of shoulder immobilizers utilize a strap around the neck or opposite shoulder to suspend the weight of the arm. The average arm weighs about ten pounds. Thus, when prior art braces and slings are used a force of about ten pounds can be applied to the neck or opposite shoulder. This method of suspending the weight can create neck and shoulder pain, fatigue, and discomfort in a short period of time.

Prior art braces and slings hold the weight of the arm and forearm in suspension but fail to fully support the arm and shoulder. The hand position is generally held against the torso, so the hand of the supported arm is not in a functional position. The prior art sling can be used with an abduction pillow to support an arm. However, this two piece configuration has drawbacks. Typically, slings are assembled and fitted to the patient by the surgical team and placed on the patient's arm while they are asleep. Many patients find it difficult to get their arms into and out of the sling. This may be because the sling is made of a loose fabric that may tend to cling to and move with the patient's arm rather than a more rigid structure that is more easily separated from the arm.

In addition, prior art shoulder immobilizers provide little or no rotational stability, meaning that these devices do not stabilize the arm when the patient's body rotates out of a vertical torso orientation. Shoulder immobilizers can be functional while the patient is standing or sitting upright. However, the immobilizers can create issues of discomfort or even risk further injury when the users reposition or lie on their side in lateral decubitus. Sleeping can be very difficult after surgery or any injury of the shoulder and therefore rotational stability is very important for comfort which is necessary for proper rest and sleep while the patient is a horizontal position. Similarly, prior art shoulder immobilizers can be very uncomfortable when the patient exercises or jogs because the arm support bounces with any vertical movement. Thus, prior art shoulder immobilizers and slings can only support the weight of an arm in limited conditions and these devices fail to provide a functional, comfortable, and load-bearing support and protection of the arm when the patient is not standing or sitting upright.

What is needed is an improved arm brace that is more comfortable because it does not require a strap that wraps around the neck or shoulder and fully supports the weight of the arm with rotational stability, and allows the hand to be supported in a functional position.

SUMMARY OF THE INVENTION

The inventive arm brace is a substantial improvement over the prior art which requires that the entire weight of the arm be supported by a shoulder or a neck and can provide superior protection and support for the forearm in a functional and comfortable position. The arm brace includes a soft elastic arm pad mounted on a support plate that attached to a support structure that is secured to a side of the patient with a waist strap and leg straps. The patient's forearm can be placed on an arm pad that can be a contoured elastic foam cushion. In some embodiments, the arm pad can have a deep cut out slot that can modified or custom fitted to fit the patient's forearm. The arm pad can surround, support, and protect the forearm. The slot in the arm pad can be open on the top, supported on the side surfaces and elbow end and have an open hand end that allows the patient's hand to extend out of the arm brace so that the hand can be used for various manual tasks.

The inventive brace functions as a load-bearing column that supports the arm platform and the weight of the forearm. The structural brace mechanism can also include an upper support structure coupled to an upper portion of a hip hinge and a lower support structure coupled to a lower portion of the hip hinge. The brace mechanism can be coupled to the side of the patient and positioned with the hip hinge adjacent to the patient's hip. The upper support structure can be secured to the waist of the patient with a waist strap and the lower support structure can be secured to the thigh by one or more leg straps. The hip hinge allows the inventive brace to provide arm support while simultaneously allowing the leg to rotate about the hip joint while the patient is standing, sitting, walking, running, or performing various other bodily movements.

Thus, in contrast to the prior art slings that support the weight of the arm with a tension mechanism suspension from the neck or shoulder, the inventive arm brace supports the forearm with a load-bearing/supporting compression structural column. The arm can rest in a contoured foam cushion, sitting upon an arm platform which is supported by a movable brace structure that is connected to the upper leg and waist with straps. The contoured foam cushion arm pad, which holds the user's forearm, can be releasably coupled to the arm platform with a hook and loop mechanism. The hook or loop materials can be adhesively attached to the bottom surface of the cushion arm pad and the top surface of the arm platform. For example, a hook material can be attached to the bottom surface of the cushion and a loop material can be attached to the top surface of the arm platform or the loop material can be attached to the bottom surface of the cushion and a hook material can be attached to the top surface of the arm platform. The arm pad can be positioned at the desired orientation on the arm platform and these components can be pressed together to secure the arm pad in place.

The arm platform, which supports the weight of the user's arm and cushion, can be connected by fasteners such as nuts and bolts or other secure fastening means to the upper support structure of the brace bracket or other extension from the upper part of the brace. Thus, the arm pad and platform can be adjusted to provide a comfortable arm position that can also allow the hand to perform limited functional activities such as typing, drawing, writing, grasping, etc.

The inventive arm brace is also highly adjustable so that it can be properly fitted and used by a wide variety of patient sizes. The brace can be constructed with several elongated members that are adjustable in length and can be secured in the desired lengths. For example, a horizontal portion of the upper support structure can control the horizontal position of the arm support and arm pad. The horizontal member can be shortened to move the arm pad to be very close to the patient's torso or extended to move the arm pad away from the torso. The rotational angle of the arm pad can also be adjusted. For example, the arm pad can be placed directly against the torso to position the forearm across the torso which can support and protect the forearm.

If the patient needs to use the supported hand, the arm support and arm pad can be rotated so that the hand is positioned away from the torso so that the hand can be used to perform tasks such as typing, writing, drawing, object grasping, etc. In an embodiment, a rotational mechanism such as a swivel can be mounted between the upper support structure and the arm support. For example, the rotational mechanism or swivel can be a screw that is in a vertical orientation. The arm support can be rotated into the desired position and then the screw can be tightened to secure the arm support to the upper portion of the upper support structure.

The arm brace can also be adjusted to fit different sized users. The lower vertical portion of the upper support structure that extends between the hinge and the arm platform can be adjusted in length to properly fit the patient's hip to forearm distance. For example, vertical length of the upper support structure can be extended for taller patients and shortened for shorter patients. Similarly, the length of the lower support structure below the hinge can be adjusted in length. The vertical length of the lower support structure can be extended for taller patients and shortened for shorter patients. The brace structure can be secured to the patient with a waist strap and leg straps, that fit a wide variety of body sizes. These straps can be tightened to provide support for the brace structure.

As discussed, the brace includes a hinge that has an axis of rotation. The brace can be adjusted so that the axis of rotation is aligned with the axis of rotation of the lateral hip. The hinge can allow full hip flexion while the patient is wearing the arm brace. The hinge can also have a locking mechanism that can restrict or prevent rotation of the hinge and brace. For example, the lock can allow the brace hinge to rotated within a limited range of angles or lock the brace at any angle of flexion or in full extension. By locking the hinge of the brace, stability of the arm brace can be improved.

In other embodiments, the brace structure can be used for other applications. For example, the arm support can be replaced with a desk that can be used to support other manual devices such a computer or a stand for other tools such as soldering stations, pipe tools, etc.

BRIEF DESCRIPTION OF THE DRAWINGS

FIG. 9 illustrates a front view of an embodiment of an adjustable length member in an extended position.

FIG. 10 illustrates a side view of an embodiment of an adjustable length member in an extended position.

FIG. 11 illustrates a front view of an embodiment of an adjustable length member in a retracted position.

FIG. 12 illustrates a side view of an embodiment of an adjustable length member in a retracted position.

FIG. 13 illustrates a front view of a concentric tubular embodiment of an adjustable length member.

FIG. 14 illustrates an end view of a concentric tubular embodiment of an adjustable length member.

DETAILED DESCRIPTION

Figure 1:
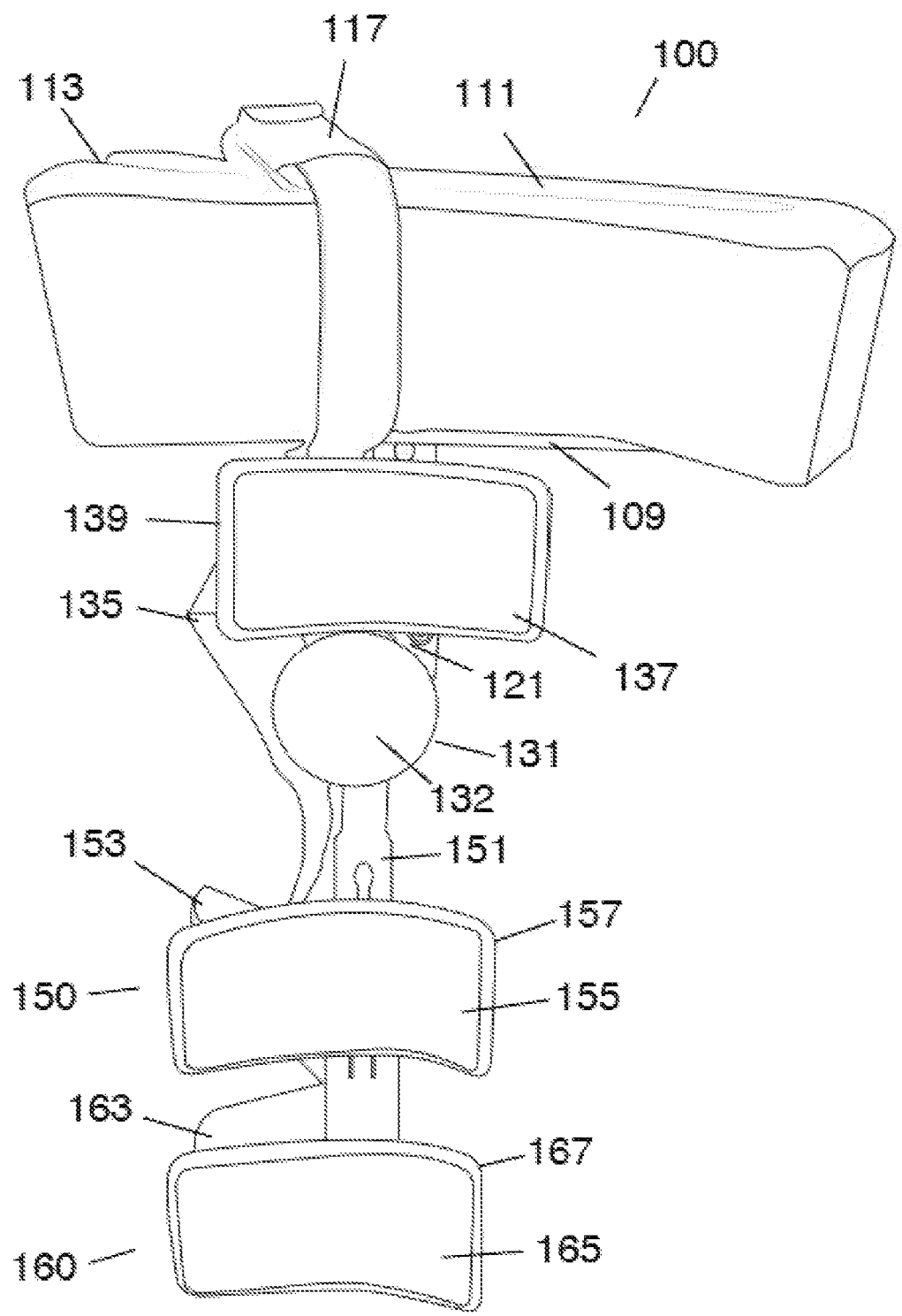
FIG. 1 illustrates a left side view of an embodiment of a right arm support with the hinge straight.
Figure 2:
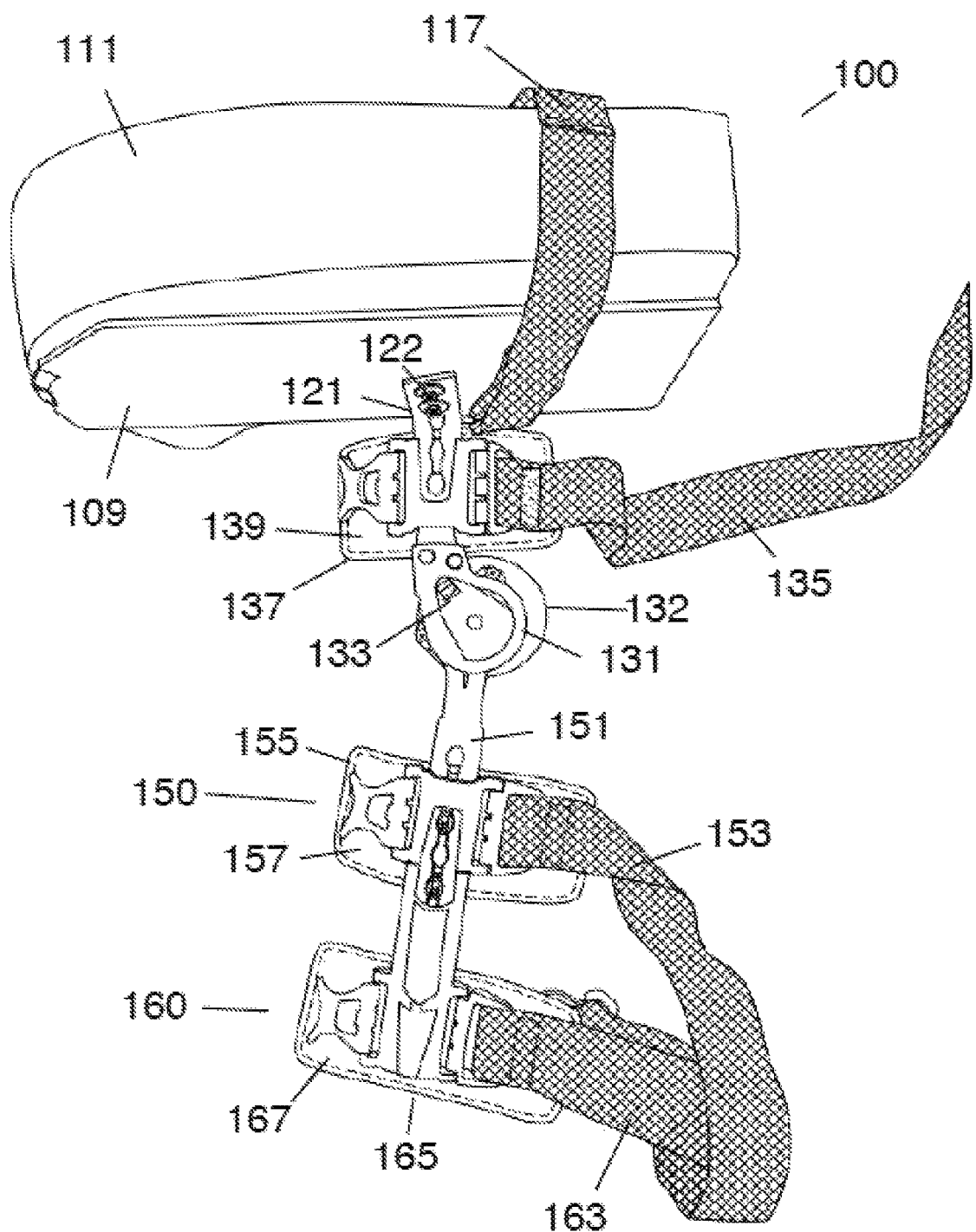
FIG. 2 illustrates a right side view of an embodiment of a right arm support with the hinge straight.
Figure 3:
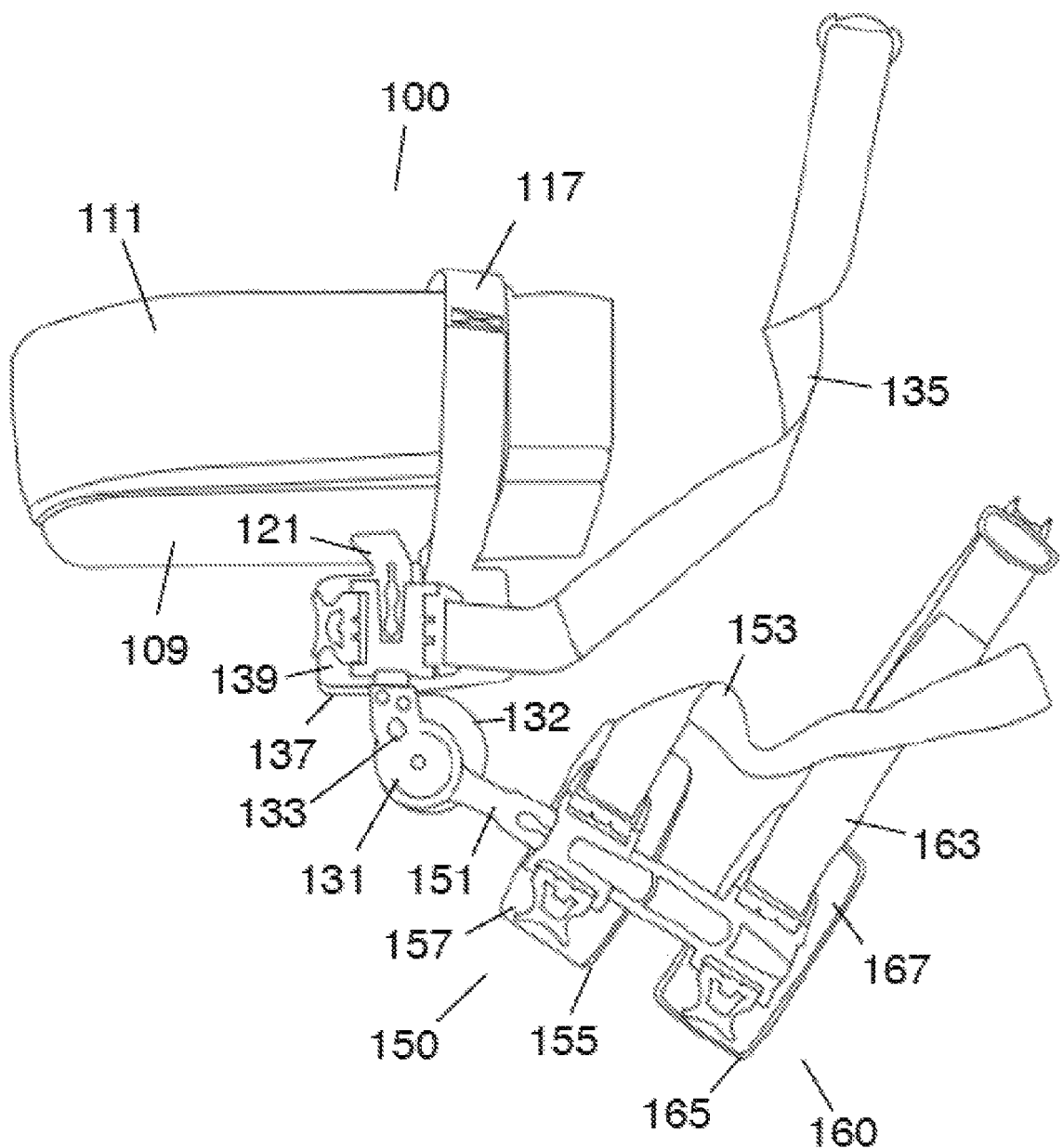
FIG. 3 illustrates a left side view of an embodiment of a right arm support with the hinge rotated.

With reference to FIGS. 1, 2, and 3, the present invention is directed towards an improved arm brace 100 for supporting the injured arm that is not supported by the patient's neck and can allow the hand supported by the brace 100 to perform functional tasks. In the illustrated embodiment, the arm brace 100 includes an arm pad 111 mounted to an upper surface of an arm support platform 109. The arm pad 111 can be made of a foam material that is covered with an elastic fabric. In an embodiment, the arm support platform 109 can be a planar structure that provides support for the entire lower planar surface of the arm pad 111. In other embodiments, the arm pad 111 and the arm support platform 109 can be any other suitable structures and shapes that can support and protect the patient's arm.

The arm pad 111 can be a thick structure that has substantially vertical side walls and planar top and bottom surfaces. The arm pad 111 can have a slot 113 that can have a shape that roughly matches the shape of the patient's forearm. When the brace 100 is worn, the forearm can be placed into the slot 113. The elbow end of the slot 113 can be closed and the hand end of the slot 113 can be opened so that the hand and fingers can extend out from the hand end of the arm pad 111. This opening can allow the hand to extend out from arm brace 100 and positioned so that the hand can be used for various tasks such as grasping items, writing, drawing, typing, etc. The slot 113 can have a "U" shaped cross section and can be shaped and contoured to support the user's forearm.

The hand end of the arm pad 111 can have detachable foam pieces that can be removed to allow the length of the slot 113 to be adjusted to properly fit the patient's forearm. A long forearm may properly fit the unmodified slot 113 in the arm pad 111. However, if the patient has a short forearm, the hand may not extend out of the open hand end of the slot 113. The arm pad 111 can have customizable features that allow it to fit a wide variety of users. For example, the arm pad 111 can have detachable pieces that can be removed so that the slot 113 of the arm pad 111 can be easily shortened to provide a proper fit.

One or more arm straps 117 can be wrapped around the arm pad 111 and the arm support platform 109 to help secure the forearm to the arm brace 100. The arm strap 117 can prevent the patient from accidentally lifting the arm out of the arm brace 100. Accidentally removing the forearm from the slot 113 of the arm pad 111 can result in a loss of protection and support and may result in injury to the limb.

The arm support platform 109 can be coupled to an upper portion of an upper support structure 121. In the illustrated embodiment, the upper support structure 121 can be an inverted "L" shaped adjustable bracket having a horizontal elongated member that can be rigidly secured to the lower surface of the arm support platform 109 and a vertical elongated member. In an embodiment, the arm support platform 109 can be rotated to any desired position on the upper portion of the upper support structure 121. For example, the arm support platform 109 can be coupled to the upper portion of the upper support structure 121 with a swivel or rotational mechanism. In an embodiment, the rotational mechanism can be a bolt or screw 122 in a vertical orientation. The bolt or screw 122 can be loosened and the arm support platform 109 can be rotated to the desired position. The bolt or screw 122 can then be tightened to secure the arm support platform 109 at the desired rotational position to the upper portion of the upper support structure 121. Additional screws can be used to further secure the arm support platform 109 to the upper portion of the upper support structure 121.

The lower portion of the upper support structure 121 can be coupled to a waist pad 137 and a waist strap 135 that is attached around a waist of the patient. A lower end of the upper support structure 121 can be coupled to an upper portion of a hip hinge 131 that can provide angular rotational support to the arm support platform 109.

As discussed, the upper support structure 121 can be an inverted "L" bracket that is formed from two elongated members that can be perpendicular to each other. Both the upper portion and the lower portion elongated members of the support structure 121 can be extendable and retractable in length. These adjustable length features can allow the arm brace 100 to be adjusted to properly fit a wide variety of patients and allow the brace supported forearm to be positioned as desired by the patient or the patient's doctor. The lower portion of the upper support structure 121 can be vertically oriented and lengthened to properly fit tall patients or shortened for shorter patients. The lower portion of the upper support structure 121 can have a locking mechanism that can used to lock the elongated structures to any desired length. For example, the elongated members can have proximal and distal portions that are secured to each other with fasteners such as screws. After the elongated members are adjusted to the desired lengths and positions, the screws can be tightened to lock the lengths of the elongated members.

As discussed, the upper portion of the upper support structure 121 is coupled to the arm support platform 109. The upper portion of the upper support structure 121 can be an elongated structure that can be horizontally oriented and can be adjustable in length to adjust the position of the supported arm pad 111. When the arm support platform 109 and the arm pad 111 need to be close to the patient, the length of the upper portion of the upper support structure 121 can be locked in a short extension. If the arm needs to be moved and/or angled away from the patient's torso the upper support structure 121 can be horizontally extended to move the arm support platform 109 away from the body. This arm position away from the patient can be useful if the hand needs to perform functions such as typing, writing, drawing, touch interactions with a user interface screen, etc.

The arm brace 100 can be coupled to a waist strap assembly that includes a waist pad 137, a support plate 139, and a waist strap 135. The waist pad 137 can be made of a soft elastic material such as foam and can have a concave cylindrical surface that can be placed against the waist of the user. A support plate 139 can be coupled to the outer convex surface of the waist pad 137. The support plate 139 can be a curved rigid structure that can distribute pressure across the entire area of the waist pad 137. The waist strap 135 can be placed against the outer convex surface of the support plate 139 so that when the waist strap 135 is tightened, the support plate 139 will compress the support plate 139 and the waist pad 137 against the patient. The waist strap 135 can be wrapped around the waist and positioned above the hips of the patient. An end of the waist strap 135 can be secured to a coupling mechanism such as a buckle, a hook/loop coupling mechanism or any other suitable fastener to the opposite end of the waist strap 135. Once the waist strap 135 is around the patient, the waist strap 135 can be tightened so that the waist pad 137 is compressed against the torso of the patient. The waist strap 135 just above hips of the patient can provide support for the arm brace 100 similar to the waist strap of a backpack.

The hinge 131 is coupled to the upper support structure 121 and a lower support structure 151. The hinge 131 can have an axis of rotation that is substantially horizontal. The hinge 131 can be placed adjacent to the patient's hip and positioned with the axis of rotation aligned with the axis rotation of the patient's hip. The hinge 131 can allow the patient's leg to rotated relative to the torso so that the arm brace 100 continues to be fully supported when the patient is standing, sitting, walking, or moving. The hinge 131 can be a thin disc shaped structure with a smooth flat surface that is faces the patient. A hinge pad 132 can be placed against hinge 131 so that the hinge pad 132 is in contact with the patient. The hinge pad 132 can be made of a soft elastic material such as elastic foam for patient comfort and to avoid abrasion.

In some embodiments, the hinge 131 can have rotation limiting controls 133 that a can be used to prevent or limit the rotation of the lower support structure 151 relative to the upper support structure 121. The rotation limiting controls 133 can be used to protect the user from over rotation of the hip joint. For example, the rotation limiting controls 133 can limit the hinge rotation between 180 degrees and 90 degrees so that the user can stand with the hinge at 180 degrees and then sit with the hinge at 90 degrees. The rotation limits can prevent the leg from being rotated backwards out of vertical alignment or into an excessive seated hip bend. In other embodiments, the rotation limiting controls 133 can allow any other rotational range or the rotation limiting controls 133 can lock the hip at a specific angular orientation.

The lower support structure 151 can be an elongated structure that is coupled to the user's leg with a first assembly 150 and a second leg strap assembly 160. In the illustrated embodiment, the first leg strap assembly 150 has a first leg strap 153, a first leg pad 155, and a first leg support plate 157. The second leg strap assembly 160 has a second leg strap 163, a second leg pad 165, and a second leg support plate 167. The leg straps 153, 163 can be wrapped around the leg and tightened to compress the support plates 157, 167 and the leg pads 155, 165 against the thigh of the patient. In some embodiments, the length of the lower support structure 151 can be adjustable so that it properly fits the patient. When the lower support structure 151 is coupled to the patient's thigh, the brace 100 has increased angular stabilization for the arm platform 109 and the arm pad 111.

With reference to FIG. 3, the brace 100 is illustrated with the hinge 131 partially rotated and the lower support structure 151 out of alignment with the upper support structure 121. The lower support structure 151 is secured to the leg and when the user's leg rotates about the hip joint, the hinge 131 allows the lower support structure 151 to move while the arm support platform 109 and arm pad 111 can remain in a substantially horizontal orientation. Thus, the arm brace 100 can bend at the hinge 131 so the user can sit down while maintaining vertical and angular support for the arm platform and the arm pad 111. This feature is very important for user functionality since the user can walk, sit, stand, or move much freely without compromising the support provided by the brace to the arm.

Figure 4:
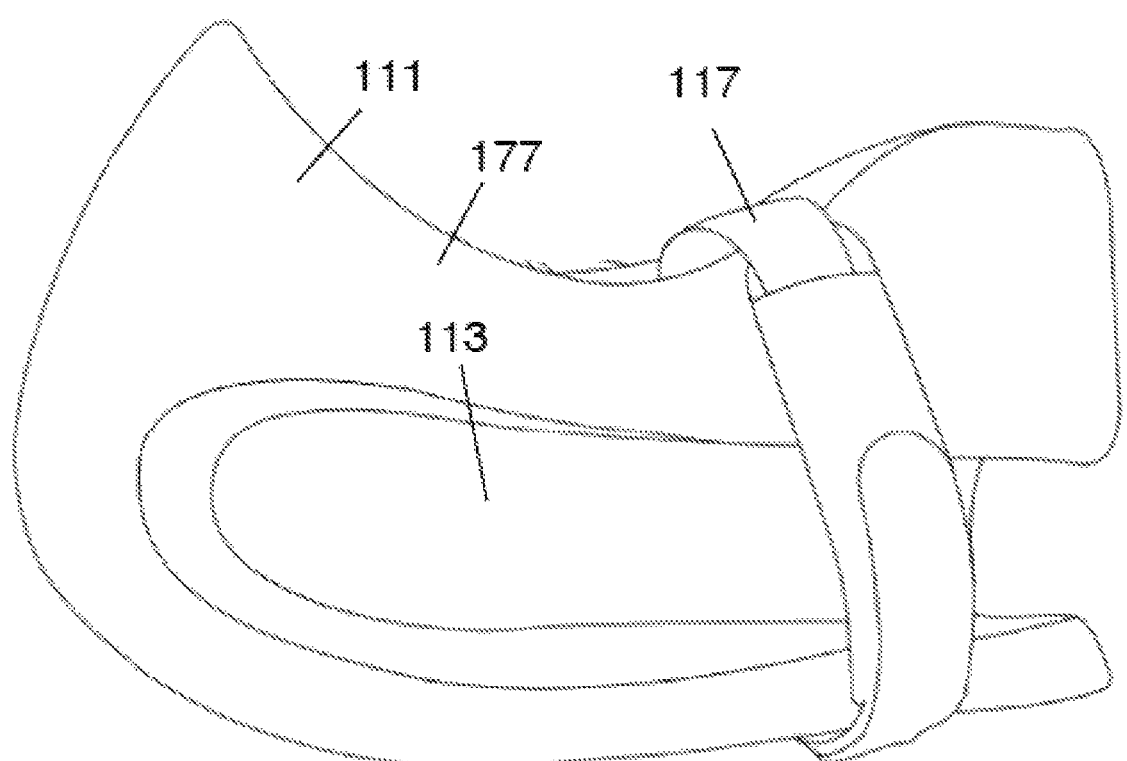
FIG. 4 illustrates a top view of an embodiment of a right arm pad.

With reference to FIG. 4, a top view of an embodiment of a right arm pad 111 is illustrated. The arm pad 111 can include a soft elastic foam pad structure that is covered with a soft elastic fabric material cover 177. The foam can be formed to the outer shape of the arm pad 111 and placed within a pocket of the fabric cover 177. The fabric cover 177 can have an internal pocket that has an internal volume that roughly matches the outer surfaces of the foam padding. The foam pad structure can tightly fit within the internal pocket of the fabric cover 177. The elastic fabric cover 177 can be made of materials such as Lycra, Spandex, or other breathable soft elastic materials. Thus, the fabric cover 177 can stretch around the foam pad so that if the user reduces or alters the size of the foam padding, the elastic fabric cover will contract and still fit tightly over the revised foam pad structure.

In the illustrated embodiment, the arm pad 111 has vertical external side surfaces, so that the arm pad has a rectangular cross section shape. In other embodiments, the arm pad 111 can have rounded convex side wall shapes or any other suitable side wall shape. The external side surface of the arm pad 111 that is adjacent to the patient can be concave and cylindrical in shape that can match the outer surface of the patient's torso. As discussed, the arm pad 111 is placed on the support platform. The concave portion of the arm pad 111 can extend over the edge of the support platform so that the support platform never comes into contact with the torso of the patient even if the concave portion of the arm pad 111 is compressed against the patient.

In the illustrated embodiment, the right arm is placed in the arm slot 113. The elbow end of the slot 113 can be padded while the hand or wrist end of the slot 113 can be opened to allow the patient's hand to extend out of the arm pad 111. The illustrated slot 113 has vertical side walls and a flat lower surface. Additional pads can be placed against the side and/or lower surfaces of the slot 113 to improve the comfort or increase the immobilization of the forearm. In other embodiments, the cross section of the slot 113 can be any other shape such as "U" shaped rather than a rectangular cross section shape. The arm pads 111 illustrated is the figures are used for right arms. If a left arm was injured, the arm pad 111 would be a mirror image with the concave side of the arm pad 111 on the opposite side.

Figure 5:
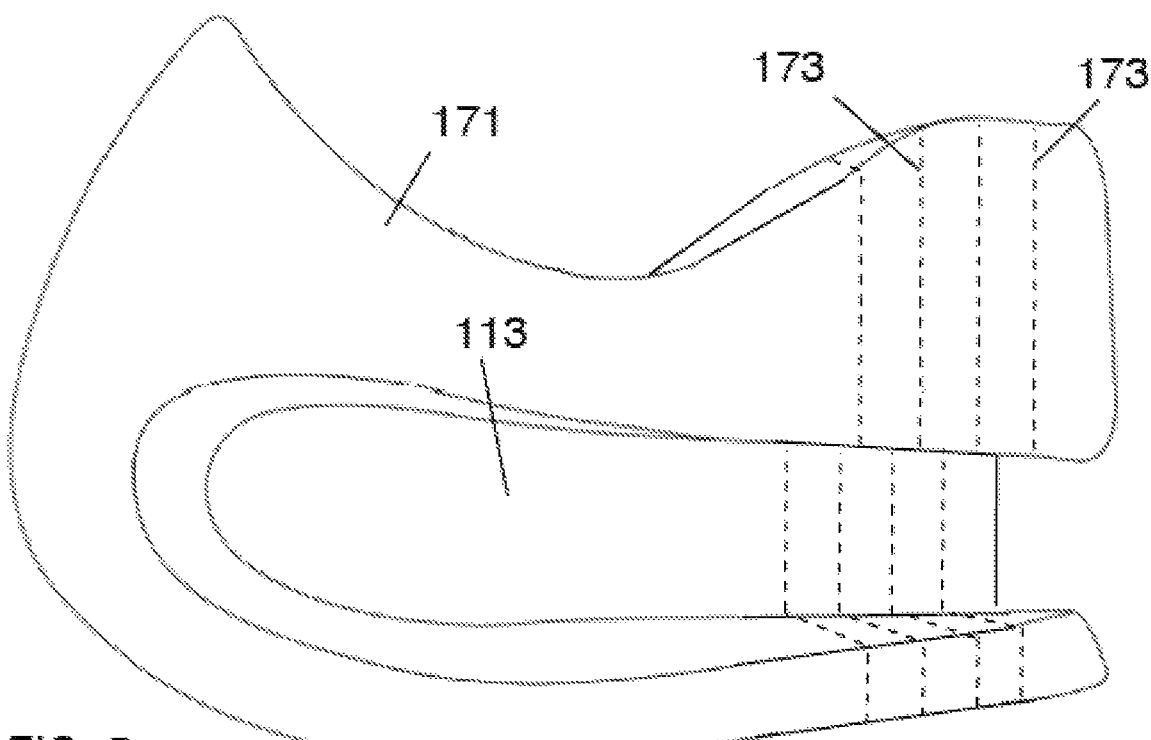
FIG. 5 illustrates a top view of an embodiment of the elastic foam of a right arm pad.

With reference to FIG. 5, a top view of the foam pad 171 separated from the fabric cover is illustrated. The arm pad 111 can be made from elastic foam such as open or closed cell foam rubber or memory foam. The open cell foam can provide more ventilation to the forearm, while the closed cell foam can provide more insulation. In some embodiments, the foam pad 171 can be easily customized to fit different sized patient forearms. For example, the foam pad 171 can initially be very long in length so that it will be large enough to fit patients having large forearms. If the foam pad 171 is used by a user with a large forearm, then no modification is required. However, if the patient's forearms is shorter and the arm pad 171 is too long, then the foam arm pad 171 can be cut and reduced in length to match the length of the patient's forearm.

In an embodiment, the hand end of the foam pad 171 can have a plurality of serrations 173 through the width of the foam pad 171 that provide cut or tear away portions at the hand end. Small portions of the foam pad 171 can be removed at the serrations 173 to make the length of the foam pad 171 shorter. The user can measure their forearm and then cut or tear the arm pad 171 at the serration 173 to adjust the length of the foam pad 171 to match the measured length of the patient's forearm. Once the size is adjusted, the foam pad 171 can be placed back into the pocket of the elastic fabric cover that can be adjusted to fit tightly over the foam arm pad.

Figure 6:
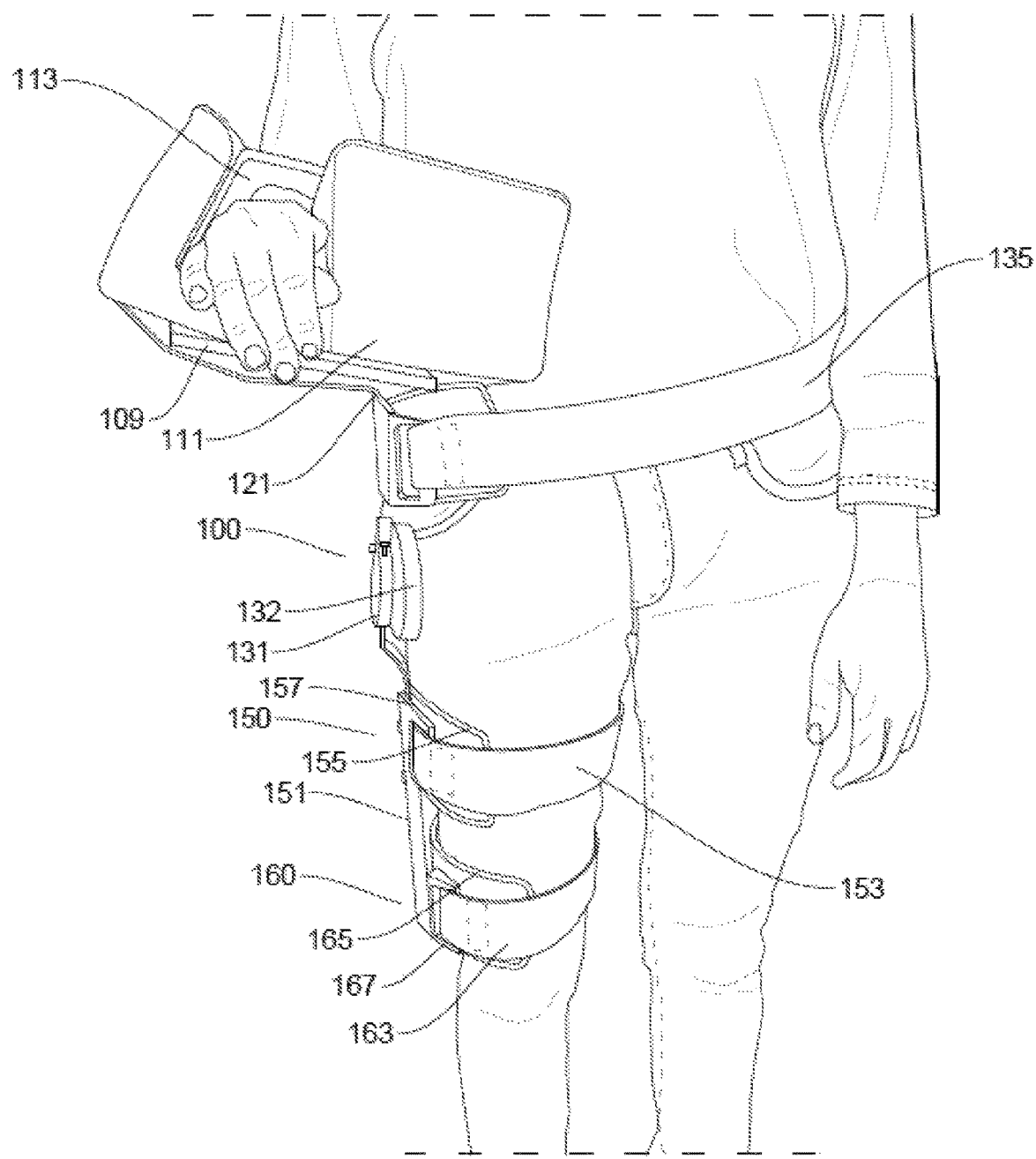
FIG. 6 illustrates a front view of a patient wearing an embodiment of the arm brace.
Figure 7:
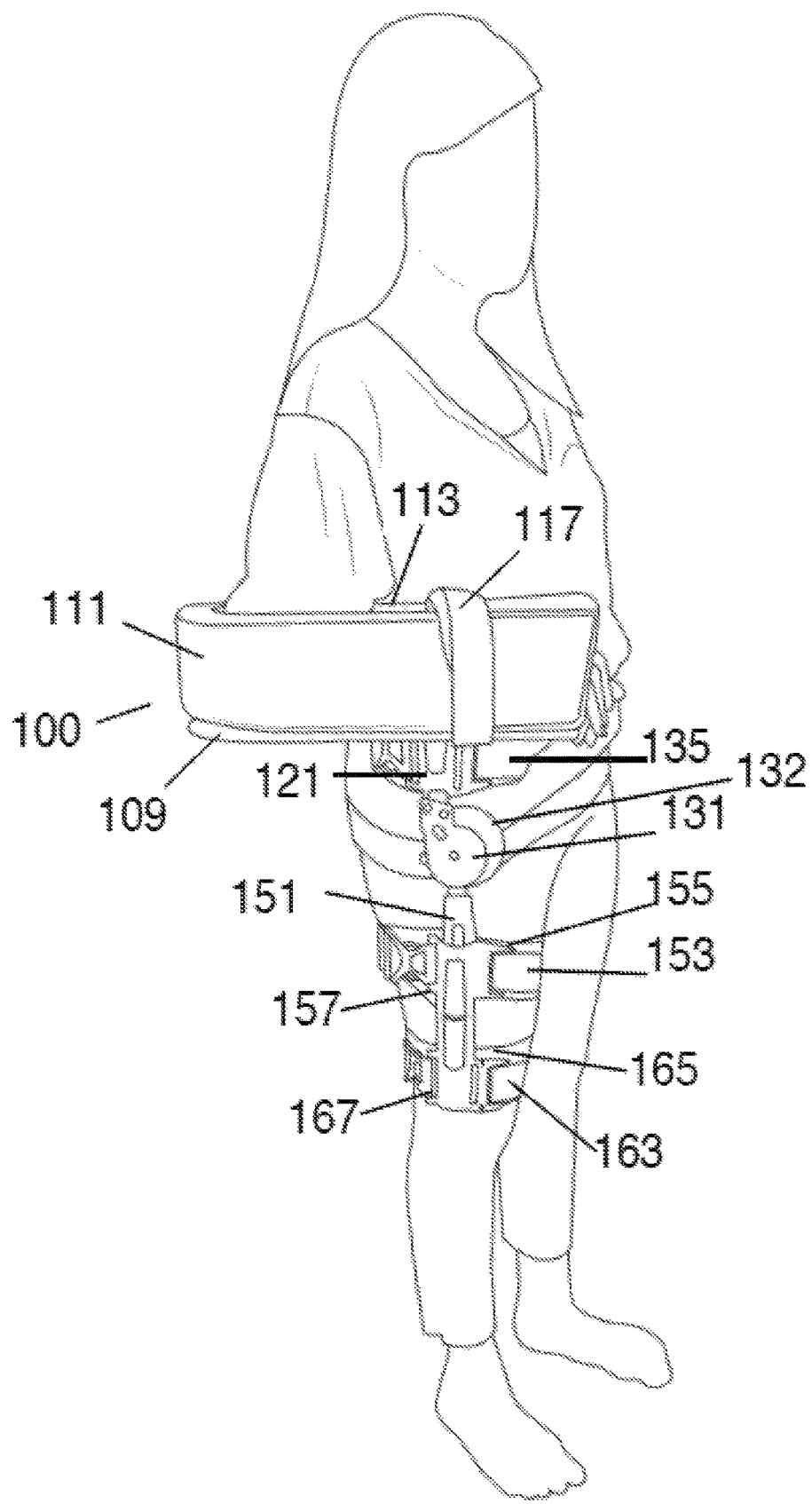
FIG. 7 illustrates a side view of a patient wearing an embodiment of the arm brace.
Figure 8:
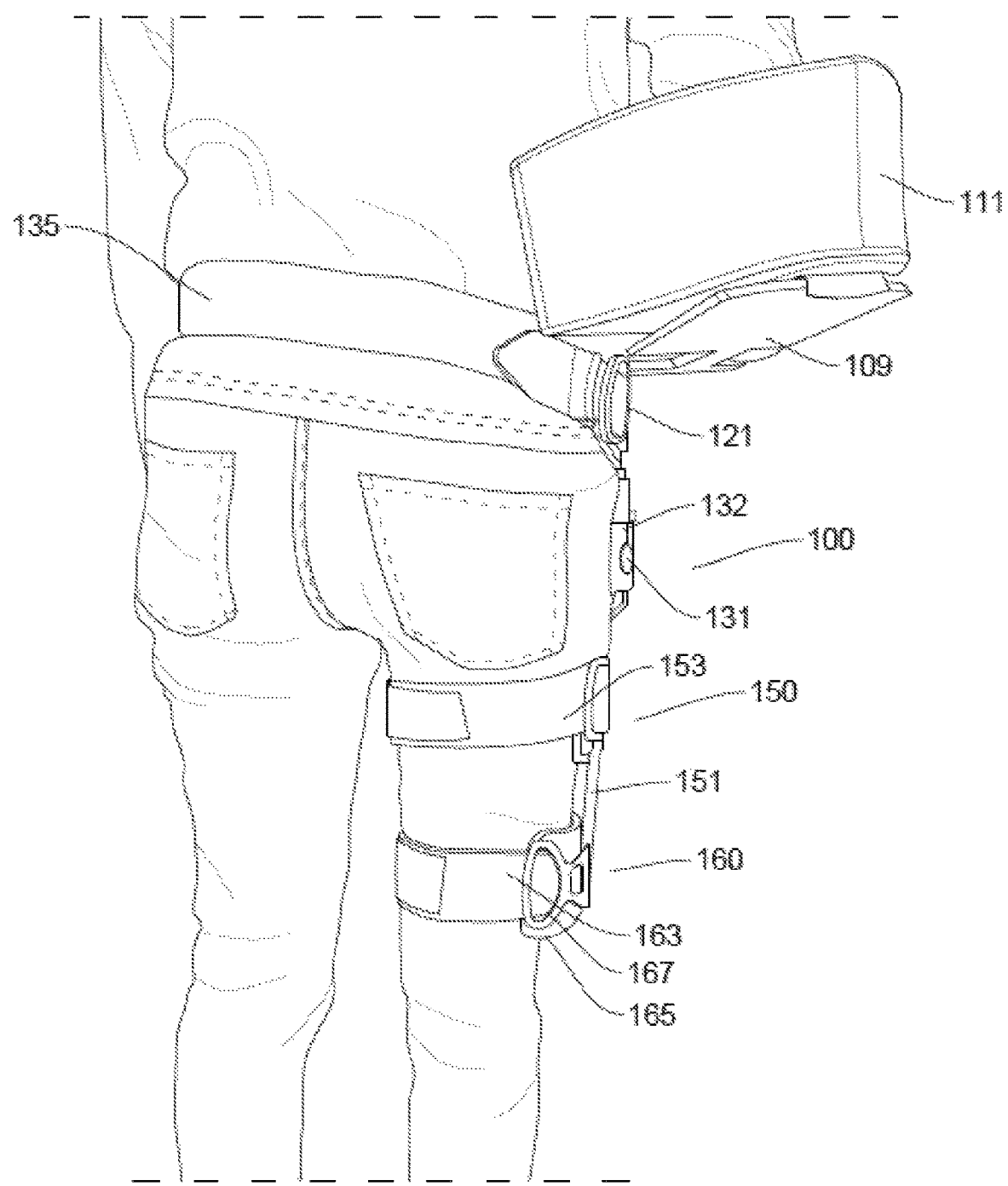
FIG. 8 illustrates a rear view of a patient wearing an embodiment of the arm brace.

FIG. 6 is a front view, FIG. 7 is a side view, and FIG. 8 is a rear view of a patient wearing an embodiment of the arm brace 100. The patient's arm is placed in the slot 113 of the arm pad 111 that rests on the arm support platform 109. The bottom of the arm support platform 109 is attached to an upper support structure 121. In the illustrated embodiment, the upper support structure 121 an inverted "L" shaped adjustable bracket which can have adjustable features that allow the position of the arm support platform 109 on the upper horizontal portion of the support structure 121 to be adjusted. This allows the user to move the horizontal position of the arm pad 111 relative to the upper support structure 121 so the arm pad 111 and arm slot 113 can be moved to a comfortable or functional position. The arm brace 100 can be configured to hold the forearm adjacent to and across the patient's torso or alternatively, the arm brace 100 can be configured to hold the forearm away from the patient's torso across with the hand end of the arm slot 113 facing away from the patient's torso.

In the illustrated embodiment, the upper portion of the upper support structure 121 bracket is a horizontal structure that can have a center slot that extends along the length. Screws or bolts can be placed through the slot and holes in the arm support platform 109. This confirmation can allow the user to adjust the position of the arm support platform 109 on the upper portion of the upper support structure 121 bracket. The screws or bolts can be tightened, when the arm support platform 109 is properly positioned on the upper portion of the upper support structure 121 bracket to lock the arm support platform 109 in place.

The lower portion of the upper support structure 121 bracket can be coupled to the upper portion of the hinge 131. A waist strap 135, a waist pad 137, and a waist support plate 139 can also be coupled to the lower portion of the upper support structure 121 bracket. The waist pad 137 is made of a soft elastic material. The inner surface of the waist pad 137 is placed against the waist of the patient and the outer surface of the waist pad 137 can be placed against the waist support plate 139 that can be coupled to the lower portion of the upper support structure 121 bracket. The waist strap 135 is wrapped around the waist of the patient and when tightened the waist strap 135 can compress the waist pad 137 and the waist support plate 139 against the waist of the patient. The waist strap 135 can function like a hip belt of a backpack and provide most of the vertical support for the arm brace 100 and the patient's arm.

The vertical elongated member that is the lower portion of the upper support structure 121 bracket can also be adjustable in length. In an embodiment, the lower portion of the upper support structure 121 bracket can have two elongated pieces that are coupled together with screw fasteners. The screw fasteners can be loosened to allow the vertical length of the upper support structure 121, the support plate 139, and the arm pad 111 to be moved to the desired vertical position to provide vertical support to the patient's forearm. The screw fasteners can then be tightened to lock the arm pad 111 at the desired vertical position.

In other embodiments, any other length adjustment mechanism can be used to adjust the horizontal and vertical lengths of the upper support structure 121 and control the position of the bracket support plate 139 and the arm pad 111. For example, the horizontal and vertical members of the upper support structure 121 bracket can be telescoping structures that can have concentric cylindrical poles with a length locking mechanism. The locking mechanism can be released to extend the lengths of the horizontal and vertical members to position the arm pad 111 at the desired horizontal and vertical positions. In some embodiments, the locking mechanism can be a quick release type clamp that can very easily be locked and released. This telescopic mechanism with quick release lever locks can be useful to allow a user to quickly and easily adjust the arm pad 111 to desired position. These types of quick release adjustments can allow easier adjustments than having to loosen fasteners, adjusting the extensions and then tightening screw type fasteners.

The hinge 131 is attached to the lower support structure 151 that can be an adjustable length elongated structure that extends down the outer side of the patient's right leg in a parallel orientation. The middle portion of the lower support structure 151 can be attached to a first leg strap assembly 150 and the lower end of the lower support structure 151 can be attached a second let strap assembly 160. The first leg strap assembly 150 can include a first leg pad 157, a first leg support plate 159, and a first leg strap 155. The second leg strap assembly 160 can include a second leg pad 167, a second leg support plate 169, and a second leg strap 165. The leg straps 155, 165 can be tightened around the thigh of the patient to compress the leg pads 157, 167 and the support plates 159, 169 against the leg. The hinge 131 and lower support structure 151 can provide vertical stability to the arm pad 111 and support plate 139 so the patient's arm is securely supported and protected by the brace 100.

The length of the lower support structure 151 can be adjusted so that the leg straps 155, 165 are positioned at comfortable locations on the leg. When the length of the lower support structure 151 is adjusted to the desired length, the screw fasteners can be tightened to lock the lower support structure 151 at the desired length. In other embodiments, any other length adjustable structures can be used such as telescoping concentric cylinders with a locking mechanism as described above.

As discussed, the upper support structure 121 and the lower support structure 151 can have elongated components that can be adjustable in length. Examples of possible adjustable length structures are illustrated in FIGS. 9-14. FIGS. 9-12 illustrates an embodiment of the adjustable length structure that is made from two flat elongated pieces 201, 203. FIGS. 9 and 10 illustrate the adjustable length structure in a lengthened configuration and FIGS. 11 and 12 illustrate the adjustable length structure in a compressed configuration.

In the first illustrated embodiment shown in FIGS. 9-12, the elongated structure can include two elongated rigid structure 201, 203 that slides against each other while the length is being adjusted. The lower structure 203 can have a slot 205 that extend along the length and the upper structure 201 can have threaded screw holes. Screw fasteners 207 can be placed through the slot 205 and screwed into the upper structure 201. The screw fasteners 207 can be loosened to adjust the length of the elongated structure and tightened to lock the length of the elongated structures.

In a second illustrated embodiment shown in FIGS. 13 and 14, the elongated structure can include an inner tube 221 and an outer tube 223 that are in a concentric telescopic configuration. A clamping ring 225 and a clamping mechanism 227 is attached to an end of the outer tube 223 that the inner tube 221 extends out of. The clamping mechanism 227 can be loosened to allow the inner tube 221 to slide within the outer tube 223. When the tubular elongated structure is adjusted to the desired length, the clamping mechanism 227 can be tightened to rigidly secure the inner tube 221 to the outer rube 223. The clamping mechanism 227 can be screw coupling, a quick release lever cam, or any other suitable clamping mechanism. The illustrated elongated structure uses circular cross section tubes. In other embodiments, the tubes can have any other cross section shape such as square, rectangular, oval, triangular, or other geometric shapes that can allow concentric sliding movement of the tubes. In other embodiments, the inventive arm brace can use any other type of adjustable elongated structure so that the arm brace can be adjusted to fit various patients and provide a wide range of arm positions.

The present invention and some of its advantages have been described in detail for some embodiments. It should be understood that although the process is described with reference to a device, system, and method the process may be used in other contexts as well. It should also be understood that various changes, substitutions, and alterations can be made herein without departing from the spirit and scope of the invention as defined by the appended claims. An embodiment of the invention may achieve multiple objectives, but not every embodiment falling within the scope of the attached claims will achieve every objective. Moreover, the scope of the present application is not intended to be limited to the particular embodiments of the process, machine, manufacture, composition of matter, means, methods, and steps described in the specification. A person having ordinary skill in the art will readily appreciate from the disclosure of the present invention that processes, machines, manufacturing steps, compositions of matter, means, methods, or steps, presently existing or later to be developed are equivalent to, and fall within the scope of, what is claimed. Accordingly, the appended claims are intended to include within their scope such processes, machines, manufacturing steps, compositions of matter, means, methods, or steps.

What is claimed is:

1. An arm support comprising:
a hip hinge having an axis of rotation;
a lower support structure coupled to a lower portion of the hip hinge;
a first leg strap coupled to the lower support structure and adapted to be secured around a thigh of a patient;
an upper support structure having an upper portion and a lower portion that is coupled to an upper portion of the hip hinge;
a waist belt coupled to the upper support structure and adapted to be secured around a waist of the patient;
an arm support platform coupled to a top portion of the upper support structure; and an arm pad coupled to an upper surface of the arm support platform;

wherein the arm support platform and the arm pad are not supported by a neck or a shoulder of the patient.

2. The arm support of claim 1 further comprising:

a second leg strap coupled to a lower portion of the lower support structure;

wherein the first leg strap is attached to the lower portion of the lower support structure and the second leg strap is attached to the lower portion of the lower support structure.

3. The arm support of claim 2 wherein the lower support structure is adjustable in length and a distance between the first leg strap and the second leg strap is increased when the lower support structure is extended in length.

4. The arm support of claim 2 wherein the lower support structure is adjustable in length and a distance between the first leg strap and the second leg strap is increased when the lower support structure is extended in length.

5. The arm support of claim 1 further comprising:

a first leg pad coupled to the first leg strap; and a waist pad coupled to the waist belt.

6. The arm support of claim 1 wherein the upper portion of the upper support structure is adjustable in length to adjust a horizontal position of the arm support platform and the arm pad.

7. The arm support of claim 1 wherein the lower portion of the upper support structure is adjustable in length to adjust a vertical position of the arm support platform and the arm pad.

8. The arm support of claim 1 wherein the axis of rotation of the hinge is parallel to a plane defined by the arm support platform.

9. The arm support of claim 1 wherein the arm pad has a concave inner side, a convex outer side, and an arm slot between the concave inner side and the convex outer side.

10. The arm support of claim 1 wherein the arm pad has a planar lower side, a concave inner side, a convex outer side, and an arm slot between the concave inner side and the convex outer side.

11. The arm support of claim 1 further comprising:

an arm pad strap that extends circumferentially around the arm pad and the arm support platform.

12. The arm support of claim 1 wherein an arm slot in the arm pad has a closed elbow end and an open wrist end.

13. The arm support of claim 1 wherein the arm pad is made of an elastic foam material that includes serrated sections at a wrist portion of the arm pad and a length of the arm pad is shortened by removing one or more of the serrated sections at the wrist portion of the arm pad.

14. The arm support of claim 1 wherein the arm pad is made of an elastic foam material that is covered with an elastic fabric.

15. The arm support of claim 1 further comprising:

a locking mechanism coupled to the hip hinge wherein the hip hinge rotates about the axis of rotation when the locking mechanism is disengaged and the hip hinge does not rotate about the axis of rotation when the locking mechanism is engaged.

16. The arm support of claim 1 further comprising:

a rotational mechanism between the arm support platform and the upper support structure that has a vertical axis of rotation, wherein the arm support platform and the arm pad rotate about the vertical axis of rotation.

17. The arm support of claim 1 wherein the upper support structure is an inverted "L" shaped bracket.

18. The arm support of claim 17 wherein the inverted "L" shaped bracket has a slot and fasteners placed through the slot that secured the arm support platform to the inverted "L" shaped bracket.

\* \* \* \* \*